(12) United States Patent
Fukuzawa et al.

(10) Patent No.: US 9,814,633 B2
(45) Date of Patent: Nov. 14, 2017

(54) PULL-ON DIAPER

(71) Applicant: UNICHARM CORPORATION, Shikokuchuo-shi, Ehime (JP)

(72) Inventors: Masumi Fukuzawa, Kanonji (JP); Shunsuke Masaki, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 279 days.

(21) Appl. No.: 14/765,838

(22) PCT Filed: Jan. 21, 2014

(86) PCT No.: PCT/JP2014/051044
§ 371 (c)(1),
(2) Date: Aug. 5, 2015

(87) PCT Pub. No.: WO2014/122980
PCT Pub. Date: Aug. 14, 2014

(65) Prior Publication Data
US 2015/0366724 A1    Dec. 24, 2015

(30) Foreign Application Priority Data

Feb. 6, 2013  (JP) ................................. 2013-021829

(51) Int. Cl.
*A61F 13/494* (2006.01)
*A61F 13/49* (2006.01)
(Continued)

(52) U.S. Cl.
CPC ...... *A61F 13/49017* (2013.01); *A61F 13/496* (2013.01); *A61F 13/49011* (2013.01);
(Continued)

(58) Field of Classification Search
CPC .......... A61F 13/49009; A61F 13/49011; A61F 13/49017; A61F 13/49019; A61F 13/4902;
(Continued)

(56) References Cited

U.S. PATENT DOCUMENTS

| 5,735,839 A  * | 4/1998 | Kawaguchi ....... A61F 13/49009 604/385.29 |
| 9,289,332 B2 * | 3/2016 | Wade ................. A61F 13/49019 |
| 2015/0051569 A1* | 2/2015 | Hashimoto ........... A61F 13/496 604/385.16 |

FOREIGN PATENT DOCUMENTS

| EP | 2387982 A1 | 11/2011 |
| EP | 2589359 A1 | 5/2013 |

(Continued)

OTHER PUBLICATIONS

Extended European Search Report in EP Application No. 14748950.4, dated Jul. 26, 2016.
(Continued)

*Primary Examiner* — Lynne Anderson
(74) *Attorney, Agent, or Firm* — Hauptman Ham, LLP (57) ABSTRACT

A pull-on diaper for younger baby has a transverse direction and a longitudinal direction, front and waist regions, a crotch region, and rear waist regions and leg cuffs extending along respective laterals of the crotch region. Each of front and rear waist panels is sectionalized into a first elastically contractible region and a second elastically contractible region wherein a dimensional ratio in the longitudinal direction between the first elastically contractible region and the second elastically contractible region is in a range of 1:1.6 to 1:2.2 and an elongation ratio of waist elastics attached to the first elastically contractible region is lower than an elongation ratio of the waist elastics attached to the second elastically contractible region and the elongation ratio of the
(Continued)

waist elastics attached to the second elastically contractible region is lower than an elongation ratio of leg cuff elastics.

6 Claims, 6 Drawing Sheets

(51) Int. Cl.
 *A61F 13/496* (2006.01)
 *A61F 13/15* (2006.01)
(52) U.S. Cl.
 CPC .. *A61F 13/49019* (2013.01); *A61F 13/49413* (2013.01); *A61F 2013/15325* (2013.01); *A61F 2013/49028* (2013.01); *A61F 2013/49092* (2013.01)
(58) Field of Classification Search
 CPC ...... A61F 13/49413; A61F 2013/15292; A61F 2013/15325; A61F 2013/49025; A61F 2013/49028; A61F 2013/49088; A61F 2013/49092; A61F 2013/4948
 See application file for complete search history.

(56) References Cited

FOREIGN PATENT DOCUMENTS

| | | |
|---|---|---|
| JP | 2001-178770 A | 7/2001 |
| JP | 2007-29479 A | 2/2007 |

OTHER PUBLICATIONS

Office Action in JP Application No. 2013-021829, dated Nov. 1, 2016.
Decision to Grant a Patent in JP Application No. 2013-021829, dated May 2, 2017.
International Search Report dated Apr. 28, 2014 in International Application No. PCT/JP2014/051044.

\* cited by examiner

PULL-ON DIAPER

RELATED APPLICATIONS

The present application is a National Phase of International Application Number PCT/JP2014/051044, filed Jan. 21, 2014, and claims priority of Japanese Patent Application No. 2013-021829 filed on Feb. 6, 2013.

TECHNICAL FIELD

The present invention relates to disposable diapers and in particular to disposable pull-on diapers adapted to younger babies.

BACKGROUND

Conventionally, pull-on diapers for infants are known. For example, Patent Literature 1 discloses a disposable pull-on diaper characterized in that each of zones substantially defined between a waist-opening's periphery and respective upper edges of leg-openings in a front waist region as well as in a rear waist region is sectionalized into three regions, namely, a waist line region, an upper flank region and a lower flank region in this order, and the respective regions are disposed with a plurality of string-like elastics extending in a width direction of the disposable diaper so that the elastics in the respective regions may have elastically contractible forces represented by a relationship of the lower flank region the upper flank region>the waist line region.

CITATION LIST

Patent Literature

{PTL 1}: JP 2001-178770 A

SUMMARY

Technical Problem

The conventional diaper for infant as disclosed in Patent Literature 1 is designed on the assumption that the diaper can be put on the infant body in upright posture or that the infant is of a growing phase in which the infant can crawl on the hands and knees. Regrettably, none of the pull-on diaper for younger babies inclusive of newborn infant has been provided. When it is tried to produce the pull-on diaper for younger babies, if the same setup values for the distribution of the elastics and the elongation ratios of the respective elastics are applied to the diaper for younger baby without any change, there will be high possibility that traces of the string-like elastics (designated hereinafter as gather traces) may be marked on the baby's skin since the muscle of the younger baby is still underdeveloped. Generally, the mother is sensitive to the health condition of her own infant and become very anxious when she becomes aware of the gather traces marked on the skin of her younger baby. From this view point, a commodity value of the diaper for younger baby considerably depends whether the skin of younger baby is liable to be marked with the gather traces or not. As another problem, if the extensible/contractile force in the lower flank region, i.e., a region put in contact with inguinal regions of the younger baby is set to the highest value as in the pull-on diaper disclosed in Patent Literature 1, the inguinal regions of the younger baby will be more liable than in the case of the wearer in an upright posture to be marked with the gather traces since the legs of the younger baby are spread in an M-shape. Meanwhile, if the extensible/contractile force adjacent to the waist-opening is set to the highest value, the diaper put on the baby's body will be liable to be displaced since the younger baby generally has a body type such that the buttocks are still underdeveloped and the abdominal region is sticking out. From the viewpoints described above, it is eagerly desired to provide the pull-on diaper assuring a fit to the body type peculiar to the younger baby and being unlikely to leave a mark on the skin of the younger baby.

An object of the present invention is to provide a pull-on diaper assuring a fit to the body type peculiar to the younger baby and being unlikely to leave a mark on the skin of the younger baby.

Solution to Problem

According to the present invention there is provided a pull-on diaper having a longitudinal direction and a transverse direction being orthogonal to each other, a skin-facing surface and a non-skin-facing surface, and including a front waist region and a rear waist region both extending in the transverse direction and a bodily-fluid absorbent panel attached to the skin-facing surface of at least the crotch region. Respective lateral portions of the front and rear waist regions are coupled with each other along a pair of seam regions extending in the longitudinal direction so that respective outer end portions of the front and rear waist regions form a waist-opening periphery and lateral portions of the crotch region form a pair of leg-openings on both sides in the transverse direction of the crotch region. The front and rear waist regions are disposed with waist elastics extending in the transverse direction contractibly attached thereto under tension. At least the crotch region is disposed with a pair of leg cuffs extending along lateral portions of the bodily-fluid absorbent panel, each of the leg cuffs has a secured edge portion and a free edge portion both extending in the longitudinal direction, and the secured edge portions are attached to the crotch region and leg cuff elastics are attached under tension to the leg cuffs along the respective free edge portions.

The pull-on diaper according to the present invention further includes the following features: when the diaper is flatly developed after the coupling of the front and rear waist regions along the seam regions has been released, each of the front and rear waist regions has a first elastically contractible region lying adjacent to the outer end and extending in the transverse direction and a second elastically contractible region lying adjacent to the first elastically contractible region and extending in the transverse direction wherein a dimensional ratio in the longitudinal direction between the first elastically contractible region and the second elastically contractible region is in a range of 1:1.6 to 1:2.2;

the leg cuff elastics are formed of elastics similar to those for the waist elastics;

the waist elastics are arranged so that, when the first and second contractible regions are stretched in the transverse direction from a non-stretched state to 90% of the maximum circumferential length, a contractile force of the second contractible region as a whole is higher than a contractile force of the first contractible region as a whole; and the elongation ratio of the waist elastics attached to the respective second elastically contractible regions is lower than an elongation ratio of the leg cuff elastics attached to the respective free edge portions and thereby a contractile force of the waist elastic attached to the respective second elastically contractible regions is lower than a contractile force of the leg cuff elastics attached to the respective free edge portions.

Advantageous Effects of Invention

With the pull-on diaper according to the present invention, each of the front and rear waist regions has the first elastically contractible region lying adjacent to the outer end and the second elastically contractible region extending adjacent to the first elastically contractible region wherein the dimensional ratio in the longitudinal direction between the first elastically contractible region lying on the outer end side and the second elastically contractible region is in a range of 1:1.6 to 1:2.2, the elongation ratio of the waist elastics attached to the first elastically contractible region is lower than the elongation ratio of the second elastically contractible region, and the elongation ratio of the waist elastics attached to the second elastically contractible region is lower than the elongation ratio of the leg cuff elastics. With such unique arrangement, the elastics having the relatively low elongation ratio intensively fit to the regions essential for leakage prevention. In this way, the pull-on diaper is adapted to fit to the body type peculiar to a younger baby and is unlikely to leave a mark on the baby's body.

DESCRIPTION OF EMBODIMENTS

Figure 1:
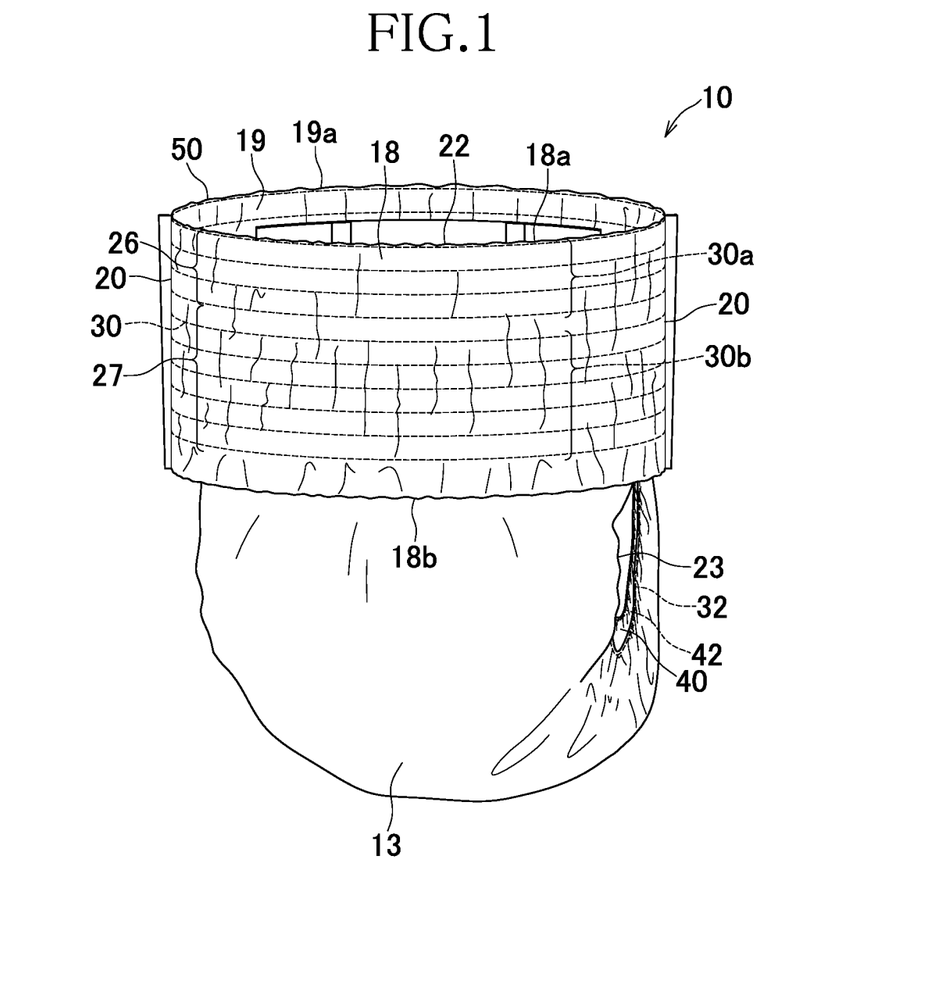
FIG. 1 is a perspective view exemplifying a pull-on diaper for younger baby according to the present invention.
Figure 2:
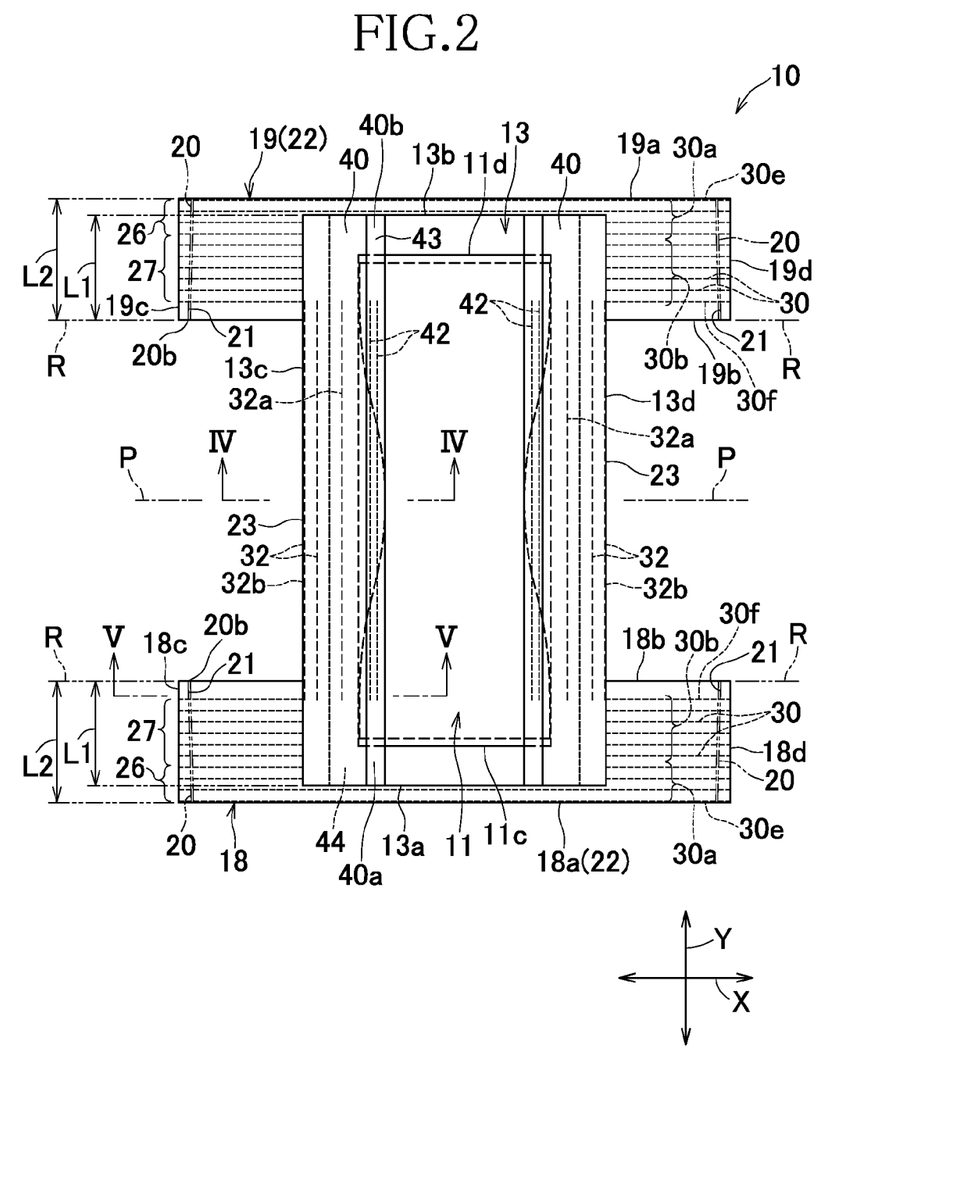
FIG. 2 is a plan view illustrating the diaper in a flatly developed state.

Referring to FIGS. 1 and 2, a diaper 10 according to the present invention has a transverse direction X and a longitudinal direction Y being orthogonal to each other, a skin-facing surface and a non-skin-facing surface, and a transverse center line P bisecting a dimension in the longitudinal direction Y, and includes a front waist panel 18 and a rear waist panel 19 both extending in the transverse direction X and a bodily-fluid absorbent panel 13 extending in the longitudinal direction Y and attached to the front waist panel 18 and the rear waist panel 19. The front waist panel 18, the rear waist panel 19 and the bodily-fluid absorbent panel 13 are respectively formed in a front waist region, a rear waist region and a crotch region. Respective lateral portions 18c, 18d and 19c, 19d of the front waist panel 18 and the rear waist panel 19 are coupled with each other in a pair of seam regions 20 to form an annular belt 50. The bodily-fluid absorbent panel 13 has front and rear end portions 13a, 13b (See FIG. 2) attached to respective midportions of the front waist panel 18 and the rear waist panel 19. The diaper 10 further includes a waist-opening periphery 22 defined by an outer end portion 18a of the front waist panel 18 and an outer end portion 19a of the rear waist panel 19 and a pair of leg-openings' peripheries 23 defined by the lateral portions 13c, 13d of the bodily-fluid absorbent panel 13, respective lateral portions of an inner end portion 18b of the front waist panel 18 and a inner end portion 19b of the rear waist panel 19.

FIG. 2 is a plan view illustrating the diaper 10 in a flatly developed state after the coupling of the front waist panel 18 and the rear waist panel 19 along the seam regions 20 of the diaper 10 as illustrated in FIG. 1 has been released. As illustrated in FIG. 2, the front waist panel 18 and the rear waist panel 19 have rectangular shapes which are the same in shape as well as in size. The front waist panel 18 has the outer end portion 18a and the inner end portion 18b both extending in the transverse direction X and lateral portions 18c, 18d extending orthogonally to the outer and inner end portions 18a, 18b. The rear waist panel 19 has the outer end portion 19a the inner end portion 19b extending in the transverse direction X and lateral portions 19c, 19d extending orthogonally to the outer and inner end portions 19a, 19b. The lateral portions 18c, 18d of the front waist panel 18 and the lateral portions 19c, 19d of the rear waist panel 19 facing each other, respectively, may be overlapped and coupled with each other with the use of the hot welding technique such as hot embossing/debossing or ultrasonic welding to define the waist-opening periphery 22 of the diaper 10 by the outer end portions 18a, 19a of the front and rear waist panels 18, 19. The front and rear waist panels 18, 19 are disposed with waist elastics 30 extending in the transverse direction X attached thereto under tension and the lateral portions 13c, 13d of the bodily-fluid absorbent panel 13 are disposed with a plurality of leg elastics 32 extending in the longitudinal direction Y contractibly attached under tension.

Figure 3:
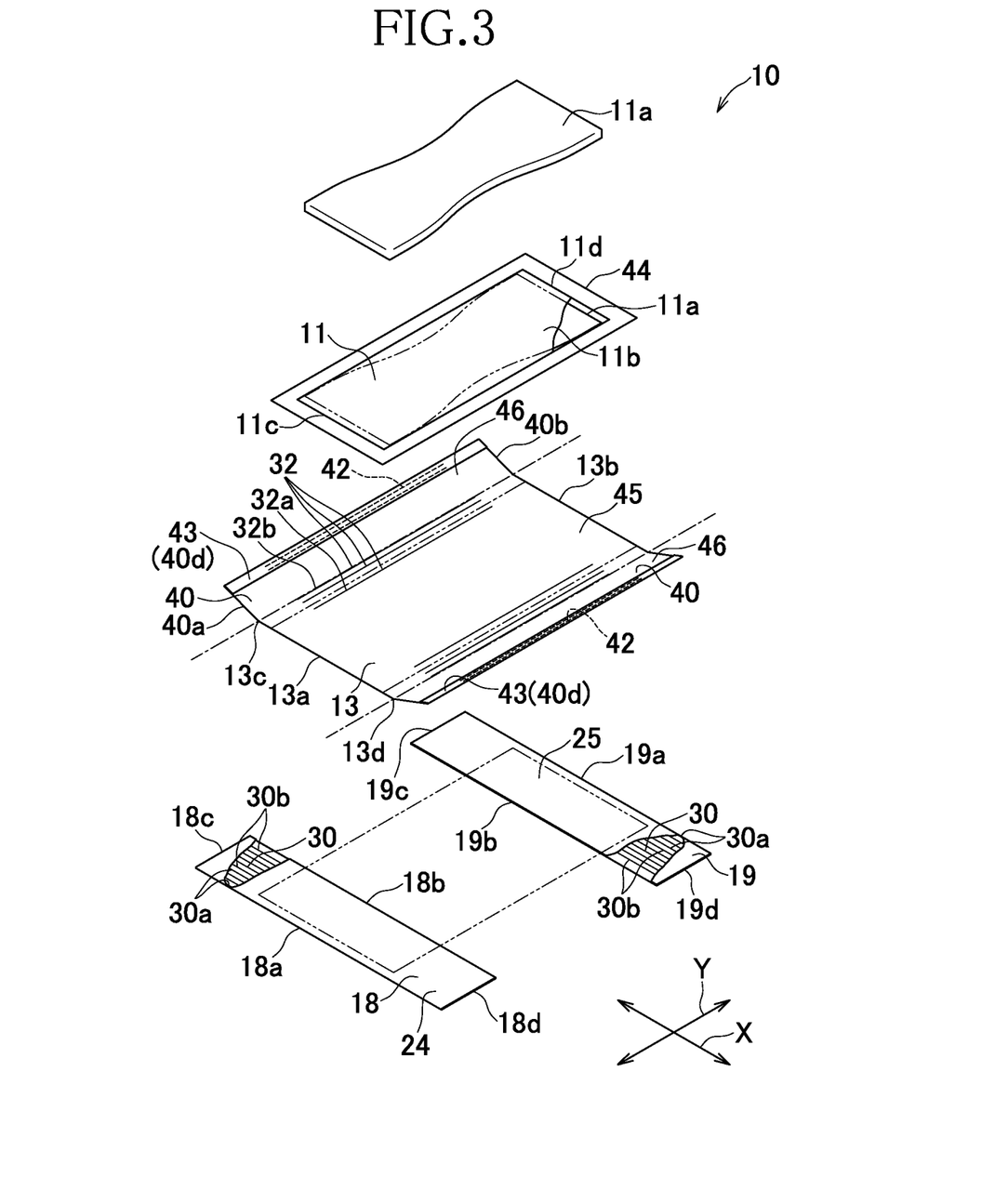
FIG. 3 is an exploded perspective view of the diaper.

Referring to FIG. 3, the front and rear waist panels 18, 19 are respectively formed from a front sheet 24 and a rear sheet 25, respectively doubled-up so as to interpose a plurality of waist elastics 30 extending in the transverse direction X between layers facing each other of the respective doubled-up sheets 24, 25 and to secure these waist elastics 30 to the respective belts 18, 19 under tension with the use of a hot melt adhesive. Alternatively, it is also possible to compose the front and rear waist panels 18, 19 from an inner sheet lying on the skin-facing surface and an outer sheet lying on the non-skin-facing surface, respectively.

The front sheet 24 and the rear sheet 25 are formed preferably of an air-permeable fibrous nonwoven fabric made of a thermoplastic resin or a plastic sheet. As the fibrous nonwoven fabric made of the thermoplastic resin or the plastic sheet, one or more may be selected from, for example, an SMS (spunbond/meltblown/spunbond) fibrous nonwoven fabric, a spunbond nonwoven fabric, an air-through nonwoven fabric and an air-permeable plastic sheet each having a mass per unit area in a range of about 15 to about 30 g/m$^2$.

The waist elastics 30 attached to the front and rear waist panels 18, 19 are composed of a plurality of first waist elastics 30a and a plurality of second waist elastics 30b. The front and rear waist panels 18, 19 respectively have first elastically contractible regions 26 defined on the side of the outer end portions 18a, 19a and disposed with the first waist elastics 30a and second elastically contractible regions 27 adjacent to the first elastically contractible regions 26, specifically, defined on the side of inner end portions 18b, 19b and disposed with the second waist elastics 30b. In an embodiment exemplified in FIG. 2, the respective first waist elastics 30a are composed of four elastics and the respective second waist elastics 30b are composed of six elastics. According to the present invention, the first elastically contractible region 26 means a region in which the first waist elastics 30a exist and the second elastically contractible region 27 means a region in which the second waist elastics 30b exist.

According to the present embodiment, a starting position of the first elastically contractible region 26 in the front waist panel 18 or the rear waist panel 19 corresponds to a position at which, of the first waist elastics 30a included in the first elastically contractible region 26 in the front waist panel 18 or the rear waist panel 19, the elastic member 30e closest to the outer end portion 18a or the outer end portion 19a extends. A boundary between the first elastically contractible region 26 and the second elastically contractible region 27 corresponds to a position at which, of the first waist elastics 30a included in the first elastically contractible region 26, the elastic closest to the second elastically contractible region 27 extends. In the front waist panel 18 illustrated in FIG. 2, for example, the first elastically contractible region 26 is the region extending from the elastic closest to the outer end portion 18a to the fourth elastics and the position at which the fourth elastic extends corresponds to the boundary between the first elastically contractible region 26 and the second elastically contractible region 27. A terminating position of the second elastically contractible region 27 corresponds to a position at which, of the second waist elastics 30b extending across the seam regions 20, the elastic member 30f closest to the inner end portion 18b of the front waist panel 18 extends. Similarly in the rear waist panel 19, a terminating position of the second elastically contractible region 27 corresponds to a position at which, of the second waist elastics 30b extending across the seam regions 20, the elastic member 30f closest to the inner end portion 19b of the rear waist panel 19 extends. According to the embodiment illustrated in FIG. 2, of the first waist elastics 30a, the waist elastics 30e respectively closest to the outer end portions 18a, 19a of the front and rear waist panels 18, 19 extend substantially so as to overlap the outer end portions 18a, 19a, respectively. Meanwhile, of the second waist elastics 30b, the waist elastics 30f closest to the inner end portions 18b, 19b extend in the transverse direction X at a distance in a range of 5 to 10 mm from the inner end portions 18b, 19b, respectively. The inner end portions 18b, 19b are at an appropriate distance from the respective waist elastics 30f in this manner and, in consequence, the inner end portions 18b, 19b formed of a nonwoven fabric function as flexible frill which softly fits to the skin of the younger baby, thereby alleviating irritation to the skin of the younger baby. As used herein, the term "younger baby" refers to an early month old child, more specifically, one from first to twelve month old child, especially one under eight month old before standing up or crawling about on one's hands and knees.

A dimensional ratio between the first elastically contractible region 26 and the second elastically contractible region 27 is in a range of 1:1.6 to 1:2.2, preferably in a range of 1:1.7 to 1:2.1. The dimensional ratio between the first elastically contractible region 26 and the second elastically contractible region 27 may be set to such values to ensure that, with the diaper 10 put on the wearer's body, the first elastically contractible region 26 is positioned slightly below the abdomen of the younger baby and the second elastically contractible region 27 is positioned in the proximity of both spurs of pelvis (iliac crests) of the younger baby. In the flatly developed state of the diaper 10 for the younger baby according to the present application, a distance between the respective outer end portions 18a, 19a of the front and rear waist panels 18, 19 is in a range of 300 mm to 400 mm. Hence, a dimension in the longitudinal direction of the diaper 10 finished in a pull-on type is in a range of about 150 mm to about 200 mm.

In the flatly developed state of the diaper 10, the elongation ratio of the first waist elastics 30a is lower than the elongation ratio of the second waist elastics 30b. In this regard, the elongation ratio represents the ratio of a length of the elastics in its elongated state to a length of the same elastics in its non-elongated state. The elongation ratio of both the first waist elastics 30a and the second waist elastics 30b is preferably in a range of 2.2 to 2.3 and, in this range, a value of the elongation ratio of the first waist elastics 30a is preferably set to a value of the elongation ratio lower than a value of elongation ratio of the second waist elastics 30b. In the conventional pull-on diaper, in contrast, a value of the elongation ratio of the first waist elastics 30a is typically higher than a value of the elongation ratio of the second waist elastics 30b. According to the present invention, the elongation ratio of the first elastically contractible region 26 adapted to be positioned at the abdominal region of the younger baby is set to be lower than the elongation ratio of the second elastically contractible region 27 adapted to be position at the lower abdominal region of the younger baby. In this way, it is possible to provide the diaper 10 which assures an appropriate fit to the body type peculiar to the younger baby, specifically, the body type having the abdominal region sticking out and the abdominal region of the younger baby should not be marked with the gather traces. If the elongation ratio of the first elastically contractible region 26 adapted to be positioned at the abdominal region of the younger baby is set to be higher than the elongation ratio of the second elastically contractible region 27, not only the abdominal region of the younger baby will be liable to be marked with the gather traces but also the diaper 10 will be liable to be displaced downward from the abdominal region toward the lower abdominal region of the younger baby.

The waist elastics 30 are composed of a plurality of strand- or string-like elastics, interposed and contractibly attached under tension between halves of the folded back front sheet 24 or the rear sheet 25 with the use of a hot melt adhesive. As a plurality of elastics, the elastics, for example, rubber strings each have a fineness in a range of 310 to 650 dtex, preferably in a range of 350 to 650 dtex may be used. The fineness of the first waist elastics 30a may be the same as or different from the fineness of the second waist elastics 30b. When relatively thick elastics are combined with a relatively fine elastic, the relatively thick elastics are preferably arranged in the second elastically contractible region 27. Of a plurality of the elastics 30a, 30b, a pitch between each pair of the adjacent first waist elastics 30a as well as a pitch between each pair of the adjacent second waist elastics 30b may be even or uneven. According to the present application, though not limiting, the first and second waist elastics 30a, 30b are preferably arranged so that, when the first and second contractible regions 26, 27 are stretched in the transverse direction X from a non-stretched state to 90% of the maximum circumferential length, a contractile force of the second contractible region 27 as a whole is higher than a contractile force of the first contractible region 26 as a whole.

Referring to FIGS. 2 and 3, the bodily-fluid absorbent panel 13 has a rectangular shape and includes a back sheet 44, an absorbent structure 11 attached to the skin-facing surface of the back sheet 44 and an outer cover 45 attached to the non-skin-facing surface of the back sheet 44. The bodily-fluid absorbent panel 13 has front and rear end portions 13a, 13b extending in the transverse direction X and lateral portions 13c, 13d extending in the longitudinal direction Y wherein the respective non-skin-facing surfaces of the front and rear end portions 13a, 13b of the bodily-fluid absorbent panel 13 are attached to midportions of the respective skin-facing surfaces of the front waist panel 18 and the rear waist panel 19 with a hot melt adhesive. According to this embodiment, the hot melt adhesive is distributed in a region defined between the front waist panel 18 and the rear waist panel 19 and between the front and rear end portions 13a, 13b of the bodily-fluid absorbent panel 13 in a pattern of stripes extending in parallel to the longitudinal direction Y (not shown). The lateral portions 13c, 13d of the bodily-fluid absorbent panel 13 are disposed with the leg elastics 32 extending in the longitudinal direction Y attached thereto under tension. Furthermore, the bodily-fluid absorbent panel 13 is disposed on the skin-facing surface thereof with a pair of leg cuffs 40 extending in parallel to the lateral portions 13c, 13d.

The back sheet 44 has an area sufficient to cover the entire non-skin-facing surface of the absorbent structure 11 and is formed of a liquid-impermeable plastic film. The outer cover 45 partially constitutes both the inner surface and the outer surface of the diaper 10 and, in view of this, this outer cover 45 is preferably formed, though not limiting, of an air-permeable and comfortable textured fibrous nonwoven fabric. The absorbent structure includes an absorbent core 11a of an hourglass-shape which is concave inward in its midsection in the longitudinal direction A and may be formed by wrapping a known bodily fluid absorptive material such as fluff wood pulp and superabsorbent polymer particles (SAP) with tissue paper and covering the core 11a with a bodyside liner 11b formed of a nonwoven fabric having liquid-permeability and flexibility. The absorbent structure 11 is attached to the skin-facing surface of the back sheet 44 with the use of hot melt adhesive. Both end portions 11c, 11d of the absorbent structure 11 overlap with respective second elastically contractible regions of the front and rear waist panels 18, 19.

Referring to FIG. 2, the both end portions, specifically, the front and rear end portions 13a, 13b of the bodily-fluid absorbent panel 13 preferably cover the respective skin-facing surfaces of the front and rear waist panels 18, 19 over a wide range as the diaper 10 flatly developed is viewed from the skin-facing surface. In such situation, the bodyside liner 11b of the nonwoven fabric having liquid-permeability and flexibility lying on the skin-facing surface of the bodily-fluid absorbent panel 13 is interposed between the waist elastics 30 attached to the front and rear waist panels 18, 19 and the skin of the younger baby in the diaper 10 put on the baby's body. In consequence, the skin of the younger baby is unlikely to be marked with the gather traces. More specifically, when the front and rear end portions 13a, 13b of the bodily-fluid absorbent panel 13 are attached to the front and rear waist panels 18, 19, respectively, in the front waist panel 18 for example, a dimension L1 in the longitudinal direction from an imaginary line R connecting inner end edges 20b closest to the transverse center line P bisecting the dimension in the longitudinal direction of the diaper 10 of a pair of the seam regions 20 to the front end portion 13a is preferably at least 70%, more preferably in a range of 70% to 95% of a dimension L2 in the longitudinal direction from the imaginary line R to the outer end portion 18a of the front waist panel 18. According to the embodiment illustrated in FIG. 2, the imaginary line R coincides with the inner end portion 18b of the front waist panel. Such dimensioning is true also in the rear waist panel 19.

Preferably, the both end portions of the absorbent structure 11, namely, the both end portions 11c, 11d are overlapped with and attached to part of the respective second elastically contractible regions 27 in the front and rear waist panels 18, 19 having the elongation ratio higher than that of the first elastically contractible regions. In this way, the bodyside liner 11b on the absorbent structure 11 is interposed between a dorsal surface of the younger baby and the respective second elastically contractible regions 27. The absorbent structure 11 effectively prevent the infant skin from being marked with the gather traces. Especially in view of the fact that the younger baby spends most of the day in a supine posture, the arrangement that the skin-facing surface of the rear waist panel 19 is covered with the rear end portion 13b of the bodily-fluid absorbent panel 13 and, in addition, the second elastically contractible 27 is covered with the absorbent structure 11 is significantly effective to inhibit a possibility that the baby's skin might be marked with the gather traces.

A dimension in the transverse direction X of the outer cover 45 constituting the bodily-fluid absorbent panel 13 is larger than the corresponding dimension of the back sheet 44 and consequently the outer cover 45 includes a pair of extension portions 46 extending outward in the transverse direction X beyond the laterals of the back sheet 44 when the outer cover 45 is lapped on and attached to the back sheet 44. The absorbent structure 11 is defined between the pair of extension portions 46. In regions of the respective extension portions 46 extending along the laterals of the back sheet 44, a plurality of the leg elastics 32 extending in the longitudinal direction Y are contractibly attached under tension to the outer cover 45 with a hot melt adhesive. The leg elastics 32 include an inside elastic 32a closest to the absorbent structure 11 as viewed in the transverse direction X and an outside elastic 32b most distant from the absorbent structure 11 as viewed in the transverse direction X.

Both lateral portions of the outer cover 45 are folded back with the skin-facing surface inside so as to form sleeves 43 within which a plurality of leg cuff elastics 42 are attached under tension to the outer cover 45 with the use of a hot melt adhesive. The sleeves 43 function as free edge portions 40d of the respective leg cuffs 40. For the leg elastics 32 and the leg cuff elastics 42, the elastics similar to those for the waist elastics 30 may be used. An elongation ratio of the leg elastics 32 and the leg cuff elastics 42 may be in a range of 2.0 to 3.5. The elongation ratio of the leg cuff elastics 42 is preferably set to be higher than the elongation ratio of the elongation ratio of the second waist elastics 30b, for example, preferably set to a value 1.1 to 1.3 higher than the elongation ratio of the second waist elastics 30b. The elongation ratio of the leg elastics 32 is also preferably set to be higher than the elongation ratio of the second waist elastics 30b and to be the same as the elongation ratio of the leg cuff elastics 42. In this way, the leg elastics 32 and the leg cuff elastics 42 are kept in contact with the thighs of the younger baby under an equivalent contractile force, making it possible to improve a leakage-preventing effect about the baby's thighs. From the other point of view, the contractile force necessary to assure a desired fit to the thighs of the younger baby may be evenly distributed to the leg elastics 32 and the leg cuff elastics 42 to improve a leak preventing effect around the legs and to avoid an anxiety that the skin of the infant might be marked with the gather traces due to the leg elastics 32 or the leg cuff elastics 42. If the elongation ratio of the leg elastics 32 is set to be higher than that of the leg cuff elastics 42, in the diaper 10 put on the younger baby, the leg cuff elastics 42 will sag and it will become difficult to keep the leg cuffs in close contact with the body of the younger baby. Consequently, not only the leakage preventing effect will be deteriorated but also urine and/or feces will be seen through the leg-openings as if leakage is occurring. In addition, the leg-openings' peripheries will be liable to be unacceptably tightened since the leg elastics 32 primarily support the absorbent structure 11. In contrast, if the elongation ratio of the leg elastics 32 is set to be lower than that of the leg cuff elastics 42, the leg elastics 32 will not be kept in close contact with the body of the younger baby, leaving gaps between the leg elastics 32 and the body of the younger baby and the leak preventing effect will be deteriorated. The leg cuff elastics 42 attached at the elongation ratio higher than that of the leg elastics 32 will necessarily cause the leg cuffs 40 to dig into the crotch of the younger baby.

It is considered here again that the younger baby spends most of the day in a supine posture and, in such posture, the legs of the younger baby spreads in an M-shape. If the conventional diaper is put on the younger baby, the infant skin is liable to be marked with the gather traces adjacent to inguinal region close to the protrusions of pelvis. However, the elongation ratio of the second waist elastics adapted to be positioned adjacent to the both protrusions of pelvis may be set to be lower than the elongation ratio of the leg cuff elastics 42 to prevent the vicinity of inguinal regions close to the pelvis protrusions from being marked with the gather traces.

Figure 4:
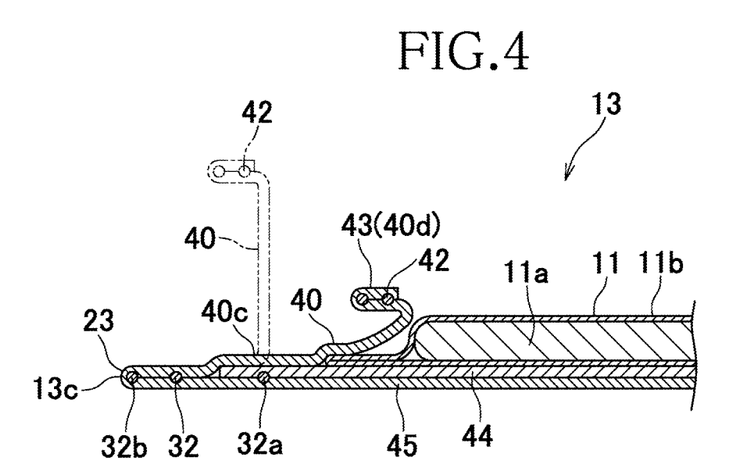
FIG. 4 is a schematic sectional view taken along line IV-IV in FIG. 2.

Referring to FIG. 4, the outer cover 45 is folded back along the outside elastic 32b with the skin-facing surface inside so as to interpose the leg elastics 32 inclusive of the inside elastic 32a and the lateral of the back sheet 44 between layers facing each other of the folded back portion of the outer cover 45. Two layers of the outer cover 45 folded back and facing each other are attached to each other with the use of hot melt adhesive in the range including the elastics from the outside elastic 32b to the inside elastic 32a. Referring to FIG. 3, folding lines of the outer cover 45 are indicated by a dashed-dotted line. With the diaper 10 put on the infant body, the regions in which the outer cover 45 has been folded back so as to interpose the outside elastic 32b under tension partially define the leg-opening peripheries 23 are kept in close contact with the thighs of the younger baby, thereby preventing leakage of bodily fluids.

Figure 5:
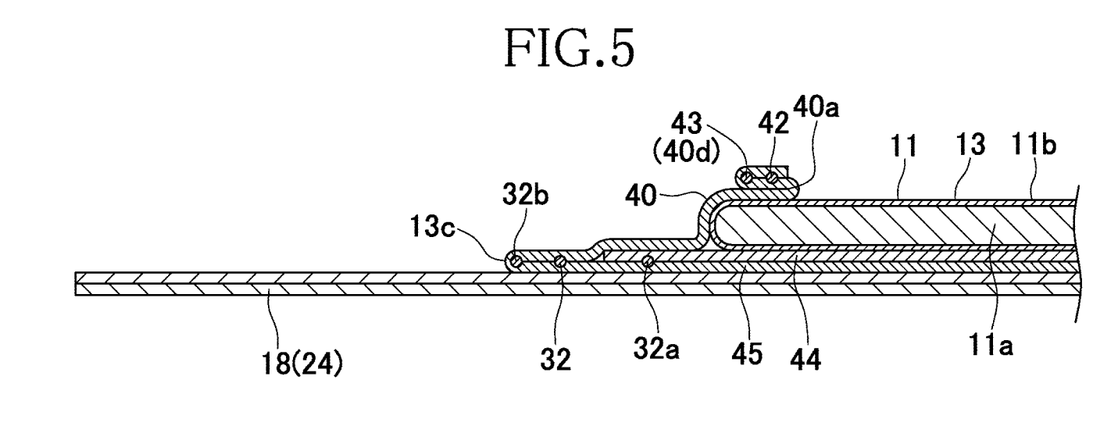
FIG. 5 is a schematic sectional view taken along line V-V in FIG. 2.

The respective inside elastics 32a among the leg elastics 32 extending in the longitudinal direction Y substantially overlap with secured edge portions 40c of the associated leg cuffs 40 as seen in the planar view. The leg cuffs 40 extend along the lateral portions 13c, 13d of the bodily-fluid absorbent panel 13 and are adapted to space away the bodyside liner 11b toward the baby's body on respective proximal end portions defined by the secured edge portions 40c. As seen in the planar view, both end portions 40a, 40b of the leg cuffs 40 overlap with the front waist panel 18 and the rear waist panel 19, respectively, and, as illustrated in FIG. 5, free edge portions 40d (sleeves 43) are folded back outward of the diaper 10 and attached to the skin-facing surface of the absorbent structure 11 with a hot melt adhesive and thereby attached to the front waist panel 18 and the rear waist panel 19. Remaining portions of the respective leg cuffs 40 are not attached to any other members and consequently space away the bodyside liner 11b toward the baby's body as indicated by imaginary lines in FIG. 4 under contraction of the leg cuff elastics 42 when the diaper 10 is put on the baby's body.

Figure 6:
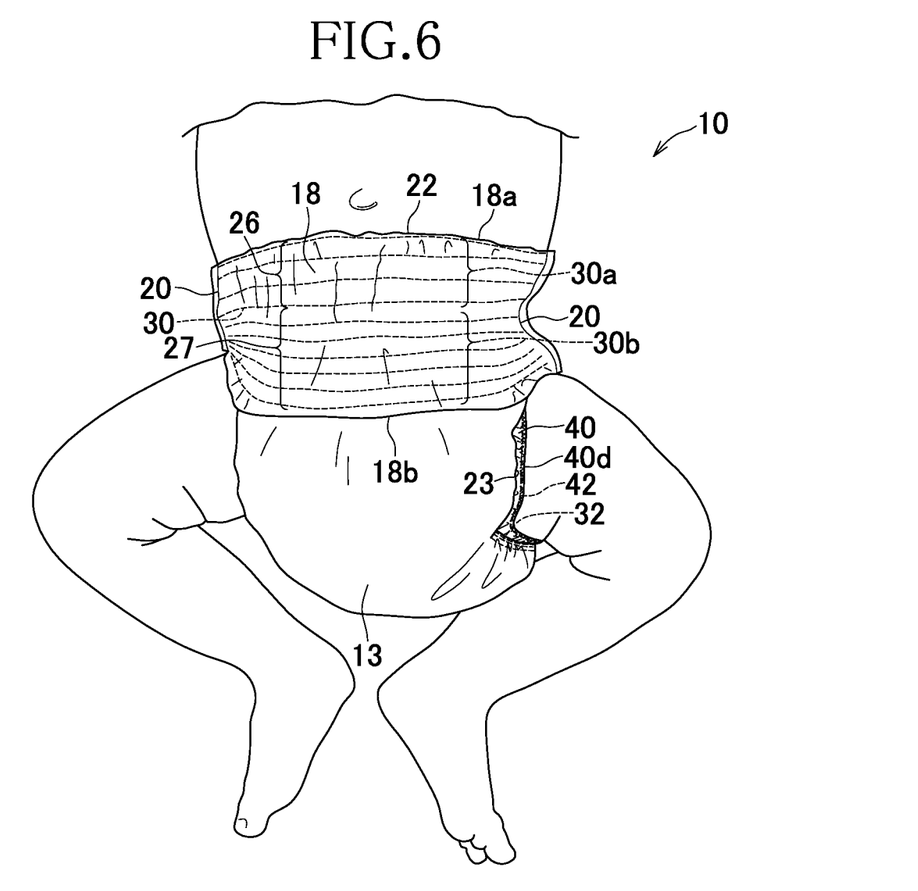
FIG. 6 is a schematic diagram illustrating a pull-on diaper for younger baby in a state put on the wearer.

The respective both end portions 40a, 40b of the leg cuffs 40 are attached to the skin-facing surface of the absorbent structure 11 preferably in regions defined between the respective outer end portions 18a, 19a and the respective inner end portions 18b, 19b of the front and rear waist panels 18, 19. In this way, it is possible to position the respective free edge portions 40d of the leg cuffs 40 just above the leg-openings' peripheries 23 in a longitudinal direction Y when the diaper 10 is shaped to the pull-on. Consequently, the respective free edge portions 40d of the leg cuffs 40 are pushed outwardly of the diaper 10 together with the legs of the younger baby through the leg-openings' peripheries 23 and stay between the legs of the younger baby and the leg-openings' peripheries 23 (See FIG. 6) when the diaper 10 is put on the infant body. Specifically, the respective free edge portions 40d of the leg cuffs 40 lie between the leg elastics 32 extending along the leg-openings' peripheries 23 and the legs of the younger baby and function as cushioning members, making it possible to prevent the legs of the younger baby from being marked with the gather traces. In addition, the leg elastics 32 cooperate with the leg cuff elastics 42 to prevent leakage beyond the leg-openings of the diaper 10.

In the diaper 10 according to the present application, a tensile load is preferably 8 N or less when the annular belt 50 as a whole formed of the front and rear waist panels 18, 19 stretched to 90% of the maximum circumferential length. On this condition, it is possible to provide the pull-on diaper 10 which alleviates a burden imposed on the hands of a mother or a care person, facilitates the belts to be expanded and the legs to be put through the leg-openings when the diaper 10 is put on the body of the younger baby. The phrase used herein "the maximum circumferential length of the annular belt 50 as a whole formed from the front and rear waist panels 18, 19" is the phrase used on the basis of a circumferential length of the waist-opening measured on an inside portion between each pair of the seam regions 20 and, in other words, the maximum circumferential length of the regions in which the respective inside portions between the pair of the seam region 20 contract in the transverse direction X to the minimal width when the diaper 10 is flatly developed.

A tensile load of the annular belt 50 as a whole according to the present application was measured by inserting a pair of hook-like tension jig positioned one above the other and gradually increasing a distance between these tension jigs. Each of the hook-like tension jigs includes a metallic square bar (3 mm in width and 5.5 mm in height) having a dimension longer than the respective widths of the front and rear waist panels 18, 19 (a dimension between the outer end portion 18a and the inner end portion 18b of the front waist panel 18) in the diaper 10. Measurement was conducted by the following steps as described below.

1) The metallic square bars are attached to upper and lower chucks of the tensile tester so that the respective metallic square bars may be held in horizontal posture.
2) A distance between the uppermost portion of the upper metallic square bar and the lowermost portion of the lower metallic square bar (designated as the distance between jigs) is adjusted so that the waist-opening of the diaper 10 can be put on the upper and lower metallic square bars without stretching the waist-opening and then the upper metallic square bar is inserted through the waist-opening 22 and the leg-opening 23. A load is set to 0 in this state.
3) The lower metallic square bar is inserted through the waist-opening 22 and then the leg-opening 23.
4) The distance between the jigs is adjusted so that the elastic having the highest elongation ratio among the waist elastics 30 runs out of any slack. In other words, the distance between the jigs is adjusted so that no tensile force acts on the waist elastics 30.

5) A stress rate of the tensile tester is set to 100 mm/min and the tensile test is started.

6) A tensile load at a moment when the distance between the jigs comes to 90% of the previously calculated maximum circumferential length of the front and rear waist panels 18, 19 as a whole is recorded.

In this measurement, AUTOGRAPH AG-I manufactured by Shimadzu Co., Ltd. in Japan was used as the tensile tester, with a load cell having 50N capacity.

While the pull-on diaper 10 for the younger baby composed of the rectangular front and rear waist panels 18, 19 and the bodily-fluid absorbent panel 13 have been exemplified above, the present invention is not limited to this. For example, the inner end portions 18b, 19b of the front and rear waist panels 18, 19 may be shaped so as to protrude downward in a trapezoidal shape or an arc-shape. While the case in which the front waist panel 18 and the rear waist panel 19 have a same dimension in the longitudinal direction Y has been described, it is also possible, for example, to shape the front and rear waist panels 18, 19 so that the rear waist panel 19 is larger than the front waist panel 18. It is also possible to use a sheet of which the front and rear waist regions and the crotch region are formed to produce the pull-on diaper 10 for a younger baby according to the present application.

The constituent members of the diaper 10 are not limited to those described in the specification but the other various types of material widely used in the relevant technical field may be used without limitation unless otherwise stated. As used herein, the term "attached with the use of a hot melt adhesive" means that the hot melt adhesive may be distributed in various well known patterns for bonding such as spiral-, dotted- or stripe-pattern unless otherwise stated. The terms "first" and "second" used in the specification and claims of the present invention are used merely to distinguish the similar elements, similar positions and the like.

The disclosure of the present invention described hereinabove may be arranged at least the following features:

A pull-on diaper having a longitudinal direction and a transverse direction being orthogonal to each other, a skin-facing surface and a non-skin-facing surface, and including: a front waist region and a rear waist region both extending in the transverse direction; and a bodily-fluid absorbent panel attached to the skin-facing surface of at least the crotch region, wherein respective lateral portions of the front and rear waist regions are coupled with each other along a pair of seam regions extending in the longitudinal direction so that respective outer end portions of the front and rear waist regions form a waist-opening periphery and lateral portions of the crotch region form a pair of leg-openings on both sides in the transverse direction of the crotch region; the front and rear waist regions are disposed with waist elastics extending in the transverse direction and contractibly attached thereto under tension; at least the crotch region is disposed with a pair of leg cuffs extending along lateral portions of the bodily-fluid absorbent panel; each of the leg cuffs has a secured edge portion and a free edge portion both extending in the longitudinal direction; the secured edge portions are attached to the crotch region; leg cuff elastics are contractibly attached under tension to the leg cuffs along the respective free edge portions; when the diaper is flatly developed after the coupling of the front and rear waist regions along the seam regions has been released, each of the front and rear waist regions has the first elastically contractible region lying adjacent to the outer end and extending in the transverse direction and the second elastically contractible region lying adjacent to the first elastically contractible region and extending in the transverse direction; a dimensional ratio in the longitudinal direction between the first elastically contractible region and the second elastically contractible region is in a range of 1:1.6 to 1:2.2;

the leg cuff elastics are formed of elastics similar to those for the waist elastics;

the waist elastics are arranged so that, when the first and second contractible regions are stretched in the transverse direction from a non-stretched state to 90% of the maximum circumferential length, a contractile force of the second contractible region as a whole is higher than a contractible force of the first contractible region as a whole;

and the elongation ratio of the waist elastics attached to the respective second elastically contractible regions is lower than an elongation ratio of the leg cuff elastics attached to the respective free edge portions and thereby a contractile force of the waist elastic attached to the respective second elastically contractible regions is lower than a contractile force of the leg cuff elastics attached to the respective free edge portions.

The present invention disclosed above may at least include the following embodiments, which may be taken in isolation from or in combination with one another:

(1) The elongation ratio of the waist elastics attached to the respective first elastically contractible regions as well as the elongation ratio of the waist elastics attached to the respective second elastically contractible regions is in a range of 2.2 to 2.3.

(2) The diaper has a transverse center line bisecting a dimension in the longitudinal direction of the diaper when the diaper is flatly developed after the coupling of the front and rear waist regions along the seam regions has been released; both end portions in the longitudinal direction of the bodily-fluid absorbent panel lie in the front waist region and the rear waist region, respectively; the front and rear waist regions respectively have imaginary lines connecting inner end edges closest to the crotch region of the pair of seam regions; and in each of the front and rear waist regions, a dimension in the longitudinal direction from the imaginary line to the end edge of the bodily-fluid absorbent panel is at least 70% of a dimension in the longitudinal direction from the imaginary line to the outer end edge of the front waist region or the rear waist region.

(3) The bodily-fluid absorbent panel is disposed with an absorbent structure and both end portions in the longitudinal direction of the absorbent structure overlap with part of the second elastically contractible regions in the front and rear waist regions, respectively.

(4) A tensile load measured when an annular belt as a whole formed of the front and rear waist regions coupled with each other has been stretched to 90% of the maximum circumferential length is 8 N or less.

(5) At least in the crotch region, leg elastics extending in the longitudinal direction are attached under tension to the bodily-fluid absorbent panel along laterals and, when the diaper is flatly developed after the coupling of the front and rear waist regions along the seam regions has been released, an elongation ratio of the leg elastics attached to the bodily-fluid absorbent panel along the lateral portions is same as the elongation ratio of the leg cuff elastics attached to the respective free edge portions.

The invention claimed is:

1. A pull-on diaper having a longitudinal direction and a transverse direction being orthogonal to each other, a skin-facing surface and a non-skin-facing surface and including:
a front waist region and a rear waist region both extending in the transverse direction;

a bodily-fluid absorbent panel attached to the skin-facing surface of at least the crotch region, wherein:

respective lateral portions of the front and rear waist regions are coupled with each other along a pair of seam regions extending in the longitudinal direction so that respective outer end portions of the front and rear waist regions form a waist-opening periphery and lateral portions of the crotch region form a pair of leg-openings on both sides in the transverse direction of the crotch region;

the front and rear waist regions are disposed with waist elastics extending in the transverse direction and contractibly attached thereto under tension;

at least the crotch region is disposed with a pair of leg cuffs extending along lateral portions of the bodily-fluid absorbent panel;

each of the leg cuffs has a secured edge portion and a free edge portion both extending in the longitudinal direction;

the secured edge portions are attached to the crotch region;

leg cuff elastics are contractibly attached under tension to the leg cuffs along the respective free edge portions;

when the diaper is flatly developed after the coupling of the front and rear waist regions along the seam regions has been released, each of the front and rear waist regions has a first elastically contractible region lying adjacent to the outer end and extending in the transverse direction and a second elastically contractible region lying adjacent to the first elastically contractible region and extending in the transverse direction;

a dimensional ratio in the longitudinal direction between the first elastically contractible region and the second elastically contractible region is in a range of 1:1.6 to 1:2.2;

the leg cuff elastics are formed of elastics similar to those for the waist elastics;

the waist elastics are arranged so that, when the first and second contractible regions are stretched in the transverse direction from a non-stretched state to 90% of the maximum circumferential length, a contractile force of the second contractible region as a whole is higher than a contractible force of the first contractible region as a whole; and the elongation ratio of the waist elastics attached to the respective second elastically contractible regions is lower than an elongation ratio of the leg cuff elastics attached to the respective free edge portions and thereby a contractile force of the waist elastic attached to the respective second elastically contractible regions is lower than a contractile force of the leg cuff elastics attached to the respective free edge portions.

2. The diaper according to claim 1, wherein, when the diaper is flatly developed after the coupling of the front and rear waist regions along the seam regions has been released, the elongation ratio of the waist elastics attached to the respective first elastically contractible regions as well as the elongation ratio of the waist elastics attached to the respective second elastically contractible regions is in a range of 2.2 to 2.3.

3. The diaper according to claim 1, wherein:
the diaper has a transverse center line bisecting a dimension in the longitudinal direction of the diaper when the diaper is flatly developed after the coupling of the front and rear waist regions along the seam regions has been released;

both end portions in the longitudinal direction of the bodily-fluid absorbent panel lie in the front waist region and the rear waist region, respectively;

the front and rear waist regions respectively have imaginary lines connecting inner end edges closest to the crotch region of the pair of seam regions; and in each of the front and rear waist regions, a dimension in the longitudinal direction from the imaginary line to the end edge of the bodily-fluid absorbent panel is at least 70% of a dimension in the longitudinal direction from the imaginary line to the outer end edge of the front waist region or the rear waist region.

4. The diaper according to claim 1, wherein the bodily-fluid absorbent panel is disposed with an absorbent structure and both end portions in the longitudinal direction of the absorbent structure overlap with part of the second elastically contractible regions in the front and rear waist regions, respectively.

5. The diaper according to claim 1, wherein a tensile load measured when an annular belt as a whole formed of the front and rear waist regions coupled with each other has been stretched to 90% of the maximum circumferential length is 8 N or less.

6. The diaper according to claim 1, wherein:
at least in the crotch region, leg elastics extending in the longitudinal direction are attached under tension to the bodily-fluid absorbent panel along lateral portions; and when the diaper is flatly developed after the coupling of the front and rear waist regions along the seam regions has been released, an elongation ratio of the leg elastics attached to the bodily-fluid absorbent panel along the lateral portions is same as the elongation ratio of the leg cuff elastics attached to the respective free edge portions.

* * * * *